US005902726A

United States Patent [19]
Kliewer et al.

[11] Patent Number: 5,902,726
[45] Date of Patent: May 11, 1999

[54] ACTIVATORS OF THE NUCLEAR ORPHAN RECEPTOR PEROXISOME PROLIFERATOR-ACTIVATED RECEPTOR GAMMA

[75] Inventors: Steven Anthony Kliewer, Cary; Jurgen M. Lehmann, Chapel Hill; Timothy M. Willson, Durham, all of N.C.

[73] Assignee: Glaxo Wellcome Inc., Research Triangle Park, N.C.

[21] Appl. No.: 09/028,988

[22] Filed: Feb. 25, 1998

Related U.S. Application Data

[63] Continuation of application No. 08/804,310, Feb. 21, 1997, abandoned, which is a continuation of application No. 08/386,394, Feb. 10, 1995, abandoned, which is a continuation-in-part of application No. 08/363,482, Dec. 23, 1994, abandoned.

[51] Int. Cl.$^6$ .......................... G01N 33/53; A61K 31/44; C07D 403/10
[52] U.S. Cl. .......................... 435/7.1; 424/1.69; 436/518; 436/536; 514/342; 546/269.7
[58] Field of Search .................. 514/342; 546/269.7; 424/1.69; 435/7.1; 436/518, 536

[56] References Cited

U.S. PATENT DOCUMENTS 5,356,913  10/1994  Colca ..................................... 514/342

FOREIGN PATENT DOCUMENTS

WO93/11235 A1  6/1993  WIPO .
WO 94/25026 A1  11/1994  WIPO .

OTHER PUBLICATIONS

J. Berger, et al., "Secreted Placental Alkaline Phosphatase: A Powerful New Quantitative Indicator of Gene Expression in Eukaryotic Cells," *Gene*, 66, pp. 1–10, 1988.

J.R. Colca and D.R. Morton, "Antihyperglycaemic Thiazolidinediones: Ciglitazone and Its Analogues," *New Antibiotic Drugs*, Chapter 24, pp. 255–261, Smith–Gordon, 1990.

A.Y. Chang, et al., "Ciglitazone, a New Hypoglycemic Agent. II. Effect on Glucose and Lipid Metabolisms and Insulin Binding in the Adipose Tissue of C57BL/6J–ob/ob and –+/? Mice," *Diabetes*, 32, pp. 839–845, Sep. 1983.

C. Dreyer, et al., "Control of the Peroxisomal β–Oxidation Pathway by a Novel Family of Nuclear Hormone Receptors," *Cell*, pp. 879–887, Mar. 1992.

M. Gottlicher, et al., "Fatty Acids Activate a Chimera of the Clofibric Acid–Activated Receptor and the Glucocorticoid Receptor," *Proc. Natl. Acad. Sci. USA*, 89, pp. 4653–4657, May 1992.

R.A. Graves, et al., "Analysis of a Tissue–Specific Enhancer: ARF6 Regulates Adipogenic Gene Expression," *Molecular and Cellular Biology*, 12, No. 3, pp. 1202–1208, 1992.

P.K.W. Harris and R.F. Kletzien, "Localization of a Piolglitazone Response Element in the Adipocyte Fatty Acid–Binding Protein Gene," *Molecular Pharmacology*, 45, pp. 439–445, 1993.

A. Hiragun, et al., "Preadipocyte Differentiation in Vitro: Identification of a Highly Active Adipogenic Agent," *J. of Cellular Physiology*, 134, pp. 124–130, 1988.

A. Ibrahimi, et al., "Evidence for a Common Mechanism of Action for Fatty Acids and Thiazolidinedione Antidiabetic Agents on Gene Expresion in Preadipose Cells," *Molecular Pharmacology*, 46, pp. 1070–1076, 1994.

I. Issemann and S. Green, "Activation of a Member of the Steroid Hormone Receptor Superfamily by Peroxisome Proliferators," *Nature*, 347, pp. 645–650, 1990.

H. Keller and W. Wahli, "Peroxisome Proliferator–Activated Receptors," *TEM*, 4, No. 9, pp. 291–296, 1993.

R.F. Kletzien, et al., "Enhancement of Adipocyte Differentiation by an Insulin–Sensitizing Agent," *Molecular Pharmacology*, 41, pp. 393–398, 1992.

S.A. Kliewer, et al., "Differential Expression and Activation of a Family of Murine Peroxisome Proliferator–Activated Receptors," *Proc. Natl. Acad. USA*, 91, pp. 7355–7359, 1994.

B. Luckow and G. Schutz, "CAT Constructions with Multiple Unique Restriction Sites for the Functional Analysis of Eukaryotic Promoters and Regulatory Elements," *Nucleic Acids Research*, 15, No. 13, pp. 5490–5498, 1987.

D.J. Mangelsdorf, et al., "A Direct Repeat in the Cellular Retinol–Binding Protein Type II Gene Confers Differential Regulation by RXR and RAR," *Cell*, 66, pp. 555–561, Aug. 1991.

J.J. Nolan, et al., "Improvement in Glucose Tolerance and Insulin Resistance in Obese Subjects Treated with Troglitazone," *New England J. of Med.*, 331, No. 18, pp. 1188–1193, Nov. 1994.

M. Pfahl, et al., "Nuclear Retinoic Acid Receptors: Cloning, Analysis, and Function," *Methods in Enzymology*, 189, pp. 256–270, 1990.

A. Schmidt, et al., "Identification of a New Member of the Steriod Hormone Receptor Superfamily That is Activated by a Peroxisome Proliferator and Fatty Acids," *Molecular Endocrinology*, 6, No. 4, pp. 1634–1641, 1992.

R.L. Sparks, et al., "Antidiabetic AD4743 Enhances Adipocyte Differentiation of 3T3 T Mesenchymal Stem Cells," *J. of Cellular Physiology*, 146, pp. 101–109, 1991.

P. Tontonoz, et al., "mPPARγ2: Tissue–Specific Regulator of an Adipocyte Enhancer," *Genes & Development*, 8, pp. 1224–1234, 1994.

(List continued on next page.)

*Primary Examiner*—Yogendra N. Gupta
*Attorney, Agent, or Firm*—Robert H. Brink

[57] ABSTRACT

The present invention provides activator compounds, including agonists, to the peroxisome proliferator-activated receptor gamma. Particular PPARγ activators are set forth, as are a pharmaceutical composition for treating diabetes, non-insulin-dependent diabetes mellitus, cardiovascular disorders, and methods for such treatment.

14 Claims, No Drawings

OTHER PUBLICATIONS

Y. Zhu, et al., "Cloning of a New Member of the Peroxisome Proliferator–Activated Receptor Gene Family from Mouse Liver," *J. of Biological Chem.*, 268, No. 36, pp. 26817–26820, 1993.

J. Berger, et al., *Gene*, 66, 1988, pp. 1–10, "Secreted Placental Alkaline Phosphatase: A Powerful New Quantitative Indicator of Gene Expression in Eukaryotic Cells".

J.R. Colca and D.R. Morton, *New Antibiotic Drugs*, Chapter 24, 1990, pp. 255–261, "Antihyperglycaemic Thiazolidinediones: Ciglitazone and Its Analogues".

A.Y. Chang, et al., *Diabetes*, vol. 32, Sep. 1983, pp. 839–845, "Ciglitazone, a New Hypoglycemic Agent. II Effect on Glucose and Lipid Metabolisms and Insulin Binding in the Adipose Tissue of C57BL/6J–ob/ob and –+/? Mice".

C. Dreyer, et al., *Cell*, vol. 68, Mar. 6, 1992, pp. 879–887, "Control of the Peroxisomal β–Oxidation Pathway by a Novel Family of Nuclear Hormone Receptors".

M. Gottlicher, et al., *Proc. Natl. Acad. Sci. USA*. vol. 89, May 1992, pp. 4653–4657, "Fatty Acids Activate a Chimera of the Clofibric Acid–Activated Receptor and the Glucocorticoid Receptor".

R.A. Graves, et al., *Molecular and Cellular Biology*, vol. 12, No. 3, Mar. 1992, pp. 1202–1208, "Analysis of a Tissue–Specific Enhancer: ARF6 Regulates Adipogenic Gene Expression".

P.K.W. Harris and R.F. Kletzien, *Molecular Pharmacology*, 45, 1994, pp. 439–445, "Localization of a Pioglitazone Response Element in the Adipocyte Fatty Acid–Binding Protein Gene".

A. Hiragun, et al., *Journal of Cellular Physiology*, 134, 1988, pp. 124–130, "Preadipocyte Differentiation in Vitro: Identification of a Highly Active Adipogenic Agent".

A. Ibrahimi, et al., *Molecular Pharmacology*, 46, 1994, pp. 1070–1076, "Evidence for a Common Mechanism of Action for Fatty Acids and Thiazolidinedione Antidiabetic Agents on Gene Expression in Preadipose Cells".

I. Issemann and S. Green, *Nature*, vol. 347, Oct. 18, 1990, pp. 645–650, "Activation of a Member of the Steriod Hormone Receptor Superfamily by Peroxisome Proliferators".

H. Keller and W. Wahli, *TEM*, vol. 4, No. 9, 1993, pp. 291–296, "Peroxisome Proliferator–Activated Receptors".

R.F. Kletzien, et al., *Molecular Pharmacology*, 41, 1992, pp. 393–398, "Enhancement of Adipocyte Differentiation by an Insulin—Sensitizing Agent".

S.A. Kliewer, et al., *Proc. Natl. Acad. Sci. USA*, vol. 91, Jul. 1994, pp. 7355–7359, "Differential Expression and Activation of a Family of Murine Peroxisome Proliferator–Activated Receptors".

B. Luckow and G. Schutz, *Nucleic Acids Research*, vol.15 No. 13, 1987, p. 5490, "CAT Constructions with Multiple Unique Restriction Sites for the Functional Analysis of Eukaryotic Promoters and Regulatory Elements".

D.J. Mangelsdorf, et al., *Cell*, vol. 66, Aug. 9, 1991, pp. 555–561, " A Direct Repeat in the Cellular Retinol–Binding Protein Type II Gene Confers Differential Regulation by RXR and RAR".

J.J. Nolan, et al., *The New England Journal of Medicine*, vol. 331, No. 18, Nov. 3, 1994, pp. 1188–1193, "Improvement in Glucose Tolerance and Insulin Resistance in Obese Subjects Treated with Troglitazone".

M. Pfahl, et al., *Methods in Enzymology*, vol. 189, 1990, pp. 256–270, "Nuclear Retinoic Acid Receptors: Cloning, Analysis, and Function".

A. Schmidt, et al., *Molecular Endocrinology*, vol. 6, No. 4, 1992, pp. 1634–1641, "Identification of A New Member of the Steriod Hormone Receptor Superfamily That is Activated by a Peroxisome Proliferator and Fatty Acids".

R.L. Sparks, et al., *Journal of Cellular Physiology*, 146, 1991, pp. 101–109, "Antidiabetic AD4743 Enhances Adipocyte Differentiation of 3T3 T Mesenchymal Stem Cells".

P. Tontonoz, et al., *Genes & Development*, 8, 1994, pp. 1224–1234, "mPPARγ2: Tissue–Specific Regulator of an Adipocyte Enhancer".

Y. Zhu, et al., *Journal of Biological Chemistry*, vol. 268, No. 36, 1993, pp. 26817–26820, "Cloning of a New Member of the Peroxisome Proliferator–Activated Receptor Gene Family from Mouse Liver".

Chawla, et al., *Endocrinology*, vol. 135, No. 2, 1994, pp. 798–800, "Peroxisome Proliferator–Activated Receptor (PPAR) γ: Adipose–Predominant Expression and Introduction Early in Adipocyte Differentiation".

Tonotonoz, et al., *Cell*, vol. 79, Dec. 30, 1994, pp. 1147–1156, "Stimulation of Adipogenesis in Fibroblasts by PPARγ2, a Lipid–Activated Transcription Factor".

Tontonoz, et al., *Nucleic Acids Res.*, 22(25), 1994, pp. 5628–5634, "Adipocyte–Specific Transcription Factor ARF6 is a Heterodimeric Complex of Two Nuclear Hormone Receptors, PPAR–γ and RXRa".

Kletzien, et al., *Mol. Pharmacol.*, 42(4), 1992, pp. 568–562, "Adipocyte Fatty Acid–Binding Protein: Regulation of Gene Expression in Vivo and in Vitro by an Insulin–Sensitizing Agent".

Cantello, et al., *Bioorganic & Medicinal Chemistry Letters*, vol. 4, No. 10, 1994, pp. 1181–1184, "The Synthesis of BRL 49653–A Novel and Potent Antihyperglycaemic Agent".

Cantello, et al., *Journal Med. Chem.*, 37, 1994, pp. 3977–3985, "[[ω–(Heterocyclylamino) alkoxy]benzyl]–2, 4–thiazolidinediones as Potent Antihyperglycemic Agents".

Ez–Zoubir Amri, et al., *The Journal of Biological Chemistry*, vol. 270, No. 5, 1995, pp. 2367–2371, "Cloning of a Protein That Mediates Transcriptional Effects of Fatty Acids in Preadipocytes".

Tontonoz, et al., *Molecular and Cellular Biology*, vol. 15, No. 1, Jan. 1995, pp. 351–357, "PPARγ2 Regulates Adipose Expression of the Phosphoenolpyruvate Carboxykinase Gene".

Ailhaud, et al., *TEM*, vol. 5, No. 3, 1994, pp. 132–136, "Hormonal Regulation of Adipose Differentiation".

ACTIVATORS OF THE NUCLEAR ORPHAN RECEPTOR PEROXISOME PROLIFERATOR-ACTIVATED RECEPTOR GAMMA

This application is a continuation of application Ser. No. 08/804,310 filed Feb. 21, 1997 and now allowed, which is a continuation of application Ser. No. 08/386,394 filed Feb. 10, 1995 and now abandoned, which is a continuation in part of application Ser. No. 08/363,482 filed Dec. 23, 1994 and now abandoned.

BACKGROUND OF THE INVENTION

Non-insulin-dependent diabetes mellitus (NIDDM) is characterized by insulin resistance of the peripheral tissues, including the skeletal muscle, liver, and adipose. The resulting hyperglycemia is often accompanied by defective lipid metabolism which can lead to cardiovascular complications such as atherosclerosis and hypertension.

Thiazolidinediones comprise a group of structurally-related antidiabetic compounds that increases the insulin sensitivity of target tissues (skeletal muscle, liver, adipose) in insulin resistant animals. In addition to these effects on hyperglycemia, thiazolidinediones also reduce lipid and insulin levels in animal models of NIDDM. Recently, the thiazolidinedione troglitazone was shown to have these same beneficial effects in human patients suffering from impaired glucose tolerance, a metabolic condition that precedes the development of NIDDM, as in patients suffering from NIDDM (Nolan et al., 1994). While their mechanism of action remains unclear, it is known that the thiazolidinediones do not cause increases in insulin secretion or in the number or affinity of insulin receptor binding sites, suggesting that thiazolidinediones amplify post-receptor events in the insulin signaling cascade (Colca and Morton, 1990, Chang et al., 1983).

Thiazolidinediones have been found to be efficacious inducers of differentiation in cultured pre-adipocyte cell lines (Hiragun et al., 1988; Sparks et al., 1991; Kletzien et al., 1992). Treatment of pre-adipocyte cell lines with the thiazolidinedione pioglitazone results in increased expression of the adipocyte-specific genes aP2 and adipsin as well as the glucose transporter proteins GLUT-1 and GLUT-4. These data suggest that the hypoglycemic effects of thiazolidinediones seen in vivo may be mediated through adipose tissue. However, as estimates of the contribution of adipose tissue to whole body glucose usage range from only 1–3%, it remains unclear whether the hypoglycemic effects of thiazolidinediones can be accounted for by changes in adipocytes. Additionally, thiazolidinediones have been implicated in appetite regulation disorders, see PCT patent application WO 94/25026 A1, and in increase of bone marrow fat content, (Williams, et al, 1993).

Peroxisome proliferator-activated receptor gamma (PPARγ) is an orphan member of the steroid/thyroid/retinoid superfamily of ligand-activated transcription factors. PPARγ is one of a subfamily of closely-related PPARs encoded by independent genes (Dreyer et al., 1992; Schmidt et al, 1992; Zhu et al., 1993; Kliewer et al., 1994). Three mammalian PPARs have been identified and termed PPARα, γ, and NUC-1. Homologs of PPARα and γ have been identified in the frog, Xenopus laevis; however, a third Xenopus PPAR, termed PPARβ, is not a NUC-1 homolog, leading to the suggestion that there may be additional subtypes in either or both species.

The PPARs are activated to various degrees by high (micromolar) concentrations of long-chain fatty acids and peroxisome proliferators (Isseman and Green, 1990; Gottlicher, 1992). Peroxisome proliferators are a structurally diverse group of compounds that includes herbicides, phthalate plasticizers, and the fibrate class of hypolipidemic drugs. While these data suggest that the PPARs are bona fide receptors, they remain "orphans" as none of these compounds have been shown to interact directly with the PPARs.

PPARs regulate expression of target genes by binding to DNA sequence elements, termed PPAR response elements (PPRE), as heterodimers with the retinoid X receptors (reviewed in Keller and Whali, 1993). To date, PPREs have been identified in the enhancers of a number of genes encoding proteins that regulate lipid metabolism including the three enzymes required for peroxisomal beta-oxidation of fatty acids, medium-chain acyl-CoA dehydrogenase, a key enzyme in mitochondrial beta-oxidation, and aP2, a lipid binding protein expressed exclusively in adipocytes. The nature of the PPAR target genes coupled with the activation of PPARs by fatty acids and hypolipidemic drugs suggests a physiological role for the PPARs in lipid homeostasis (reviewed in Keller and Whali, 1993).

Recently, a second isoform of PPARγ, termed PPARγ2, was cloned from a mouse adipocyte library (Tontonoz et al., 1994). PPARγ1 and γ2 differ in only 30 amino acids at the extreme N-terminus of the receptor and likely arise from a single gene. PPARγ2 is expressed in a strikingly adipose-specific manner and its expression is markedly induced during the course of differentiation of several preadipocyte cell lines; furthermore, forced expression of PPARγ2 was shown to be sufficient to activate the adipocyte-specific aP2 enhancer in non-adipocyte cell lines. These data suggest that PPARγ2 plays an important role in adipocyte differentiation.

Recently, the thiazolidinedione pioglitazone was reported to stimulate expression of a chimeric gene containing the enhancer/promoter of the lipid-binding protein aP2 upstream of the chloroamphenicol acetyl transferase reporter gene (Harris and Kletzien, 1994). Deletion analysis led to the identification of an approximately 30 bp region responsible for pioglitazone responsiveness. Interestingly, in an independent study, this 30 bp fragment was shown to contain a PPRE (Tontonoz et al., 1994). Taken together, these studies suggested the possibility that the thiazolidinediones modulate gene expression at the transcriptional level through interactions with a PPAR.

SUMMARY OF THE INVENTION

The present invention provides radiolabeled 5-{4-[2-(Methyl-pyridine-2-yl-amino)-ethoxy]-benzyl}-thiazolidine-2,4-dione. In another aspect, the present invention provides a method for determining whether a compound does or does not interact directly with PPAR-gamma, comprising the step of specifically binding a radiolabeled compound of this invention to the ligand binding domain o f PPAR-gamma.

In addition, the present invention provides a method for screening for compounds that will be useful for treating diabetes, impaired glucose tolerance, obesity, or a cardiovascular disorder non-insulin-dependent diabetes mellitus, comprising either the step of determining whether the compound interacts directly with PPAR gamma, or the step of determining whether the compound activates PPAR gamma. The present invention also provides a method for treating diabetes, impaired glucose tolerance, obesity, or a cardiovascular disorder non-insulin-dependent diabetes mellitus by administration of compounds identified using the screening method of this invention.

DETAILED DESCRIPTION OF THE INVENTION

We have found that certain chemical compounds including thiazolidinediones are efficacious and selective activators of the PPARγ. Furthermore, while it has been shown that the PPARs are activated by micromolar concentrations of fatty acids and hypolipidemic drugs such as clofibric acid and Wy14,643 (Isseman et al, 1990, Dreyer et al, 1992, Schmidt et al, 1992, Kliewer et al. 1994, Gottlicher et al, 1992), none of these compounds has been shown previously to interact directly with the PPARs. However, we have discovered that thiazolidinediones can bind directly with the PPARγ.

These data show that PPARγ is the molecular target for the therapeutic effects of these compounds on insulin resistance, NIDDM and lipid metabolism with its implications for cardiovascular disease. The identification of novel PPARγ-selective activators may lead to more effective drugs for the treatment of NIDDM and obesity as well as associated cardiovascular complications such as atherosclerosis, hypertension.

Preferably, the invention comprises an activator of PPARγ selected from the group consisting of formula (I)–(XIII):

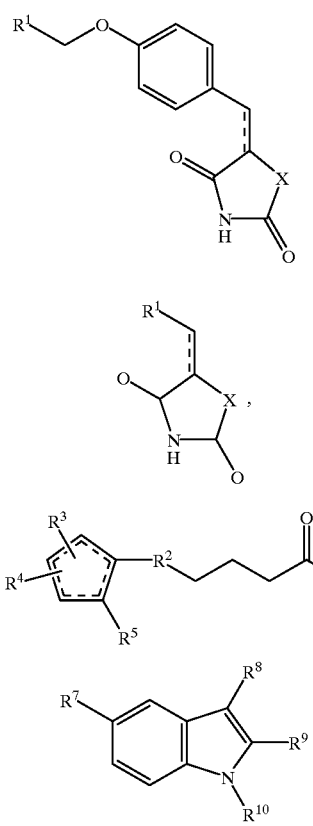

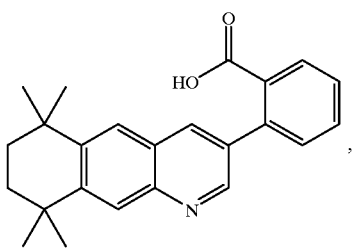

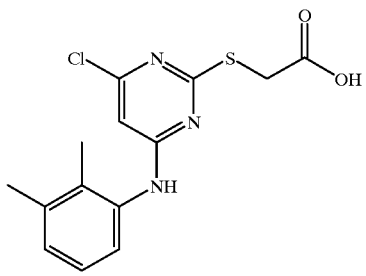

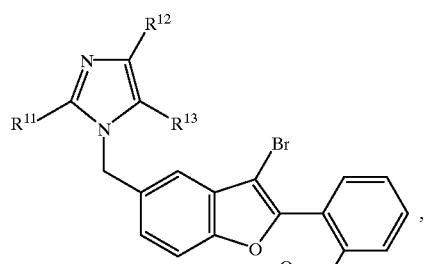

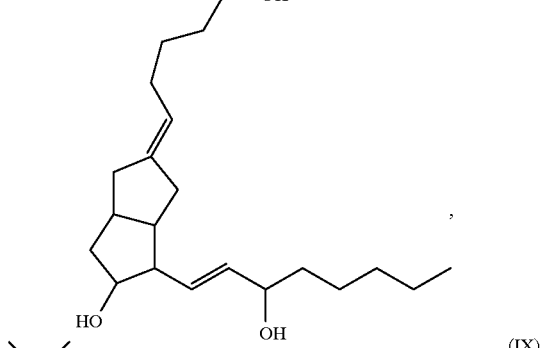

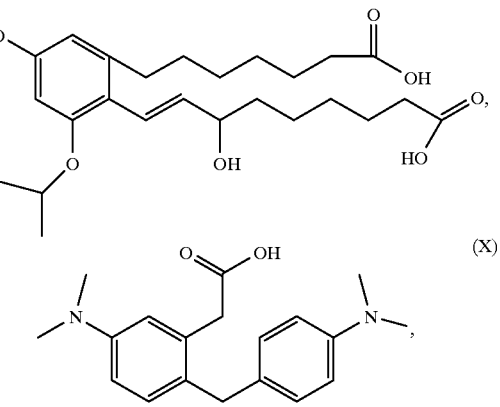

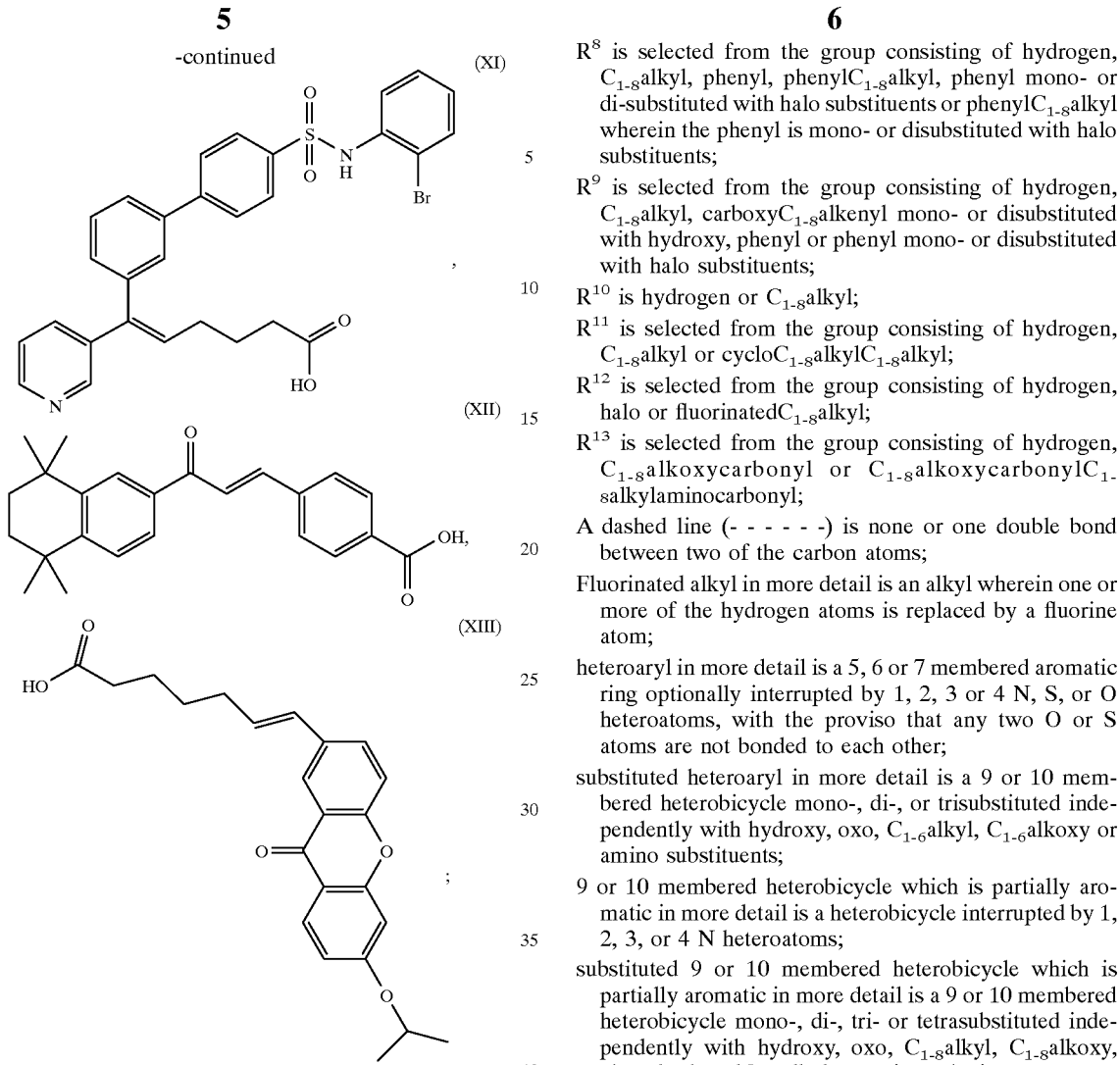

wherein:
R¹ is selected from the group consisting of hydrogen, $C_{1-8}$alkyl, amino$C_{1-8}$alkyl, $C_{1-8}$alkylamino$C_{1-8}$alkyl, heteroarylamino$C_{1-6}$alkyl, (heteroaryl)($C_{1-8}$alkyl) amino$C_{1-6}$alkyl, ($C_{1-8}$cycloalkyl)$C_{1-8}$alkyl, $C_{1-8}$alkylheteroaryl$C_{1-8}$alkyl, 9 or 10 membered heterobicycle which is partially aromatic or substituted 9 or 10 membered heterobicycle which is partially aromatic;

X is selected from the group consisting of S, NH or O;

R² is selected from the group consisting of hydrogen, $C_{1-8}$alkyl or $C_{1-8}$alkenyl;

R³ and R₄ are independently selected from the group consisting of hydrogen, hydroxy, oxo, $C_{1-8}$alkyl, $C_{1-8}$alkoxy or amino;

R⁵ is selected from the group consisting of hydrogen, $C_{1-8}$alkyl, $C_{1-8}$alkenyl, (carbonyl)alkenyl, (hydroxy)alkenyl, phenyl, $C_{1-8}$alkylR⁶, (hydroxy)$C_{1-8}$alkylR⁶, $C_{1-8}$alkyl$C_{1-8}$cycloalkylR⁶, (hydroxy)$C_{1-8}$alkyl$C_{1-8}$cycloalkylR⁶ or $C_{1-8}$cycloalkylthioR⁶;

R⁶ is selected from the group consisting of phenyl or phenyl substituted with hydroxy, $C_{1-8}$alkyl or $C_{1-8}$alkoxy substituents;

R⁷ is selected from the group consisting of hydrogen, hydroxy, carboxy or carboxy$C_{1-8}$alkyl;

R⁸ is selected from the group consisting of hydrogen, $C_{1-8}$alkyl, phenyl, phenyl$C_{1-8}$alkyl, phenyl mono- or di-substituted with halo substituents or phenyl$C_{1-8}$alkyl wherein the phenyl is mono- or disubstituted with halo substituents;

R⁹ is selected from the group consisting of hydrogen, $C_{1-8}$alkyl, carboxy$C_{1-8}$alkenyl mono- or disubstituted with hydroxy, phenyl or phenyl mono- or disubstituted with halo substituents;

R¹⁰ is hydrogen or $C_{1-8}$alkyl;

R¹¹ is selected from the group consisting of hydrogen, $C_{1-8}$alkyl or cyclo$C_{1-8}$alkyl$C_{1-8}$alkyl;

R¹² is selected from the group consisting of hydrogen, halo or fluorinated$C_{1-8}$alkyl;

R¹³ is selected from the group consisting of hydrogen, $C_{1-8}$alkoxycarbonyl or $C_{1-8}$alkoxycarbonyl$C_{1-8}$alkylaminocarbonyl;

A dashed line (- - - - -) is none or one double bond between two of the carbon atoms;

Fluorinated alkyl in more detail is an alkyl wherein one or more of the hydrogen atoms is replaced by a fluorine atom;

heteroaryl in more detail is a 5, 6 or 7 membered aromatic ring optionally interrupted by 1, 2, 3 or 4 N, S, or O heteroatoms, with the proviso that any two O or S atoms are not bonded to each other;

substituted heteroaryl in more detail is a 9 or 10 membered heterobicycle mono-, di-, or trisubstituted independently with hydroxy, oxo, $C_{1-6}$alkyl, $C_{1-6}$alkoxy or amino substituents;

9 or 10 membered heterobicycle which is partially aromatic in more detail is a heterobicycle interrupted by 1, 2, 3, or 4 N heteroatoms;

substituted 9 or 10 membered heterobicycle which is partially aromatic in more detail is a 9 or 10 membered heterobicycle mono-, di-, tri- or tetrasubstituted independently with hydroxy, oxo, $C_{1-8}$alkyl, $C_{1-8}$alkoxy, phenyl, phenyl$C_{1-8}$alkyl or amino substituents;

or a pharmaceutically acceptable acid-addition or base-addition salt thereof.

More preferably, the PPARγ activator is selected from the group consisting of formula (I) or (II):

wherein:
R¹ is selected from the group consisting of hydrogen, $C_{1-8}$alkyl, amino$C_{1-8}$alkyl, $C_{1-8}$alkylamino$C_{1-8}$alkyl, heteroarylamino$C_{1-6}$alkyl, (heteroaryl) ($C_{1-8}$alkyl)

aminoC$_{1-6}$alkyl, (C$_{1-8}$cycloalkyl)C$_{1-8}$alkyl, C$_{1-8}$alkylheteroaryllC$_{1-8}$alkyl, 9 or 10 membered heterobicycle which is partially aromatic or substituted 9 or 10 membered heterobicycle which is partially aromatic;

A dashed line (- - - - - -) is none or one double bond between the two carbon atoms.

PHARMACOLOGY

While it is possible that, for use in therapy, a compound of the invention may be administered as the raw chemical it is possible to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be acceptable in the sense of being compatable with the other ingredients of the formulation and not deleterious to the recipient thereof. According to another aspect of the invention, there is provided a process for the preparation of a pharmaceutical formulation comprising admixing a compound of formula (I) or a pharmaceutically acceptable salt or solvate thereof with one of more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical (including buccal and sublingual), vaginal or parental (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets, or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintegrants, or wetting agents. The tablets may be coated according to methods well known in the art. Timed release formulations which are known in the art may also be suitable. Oral liquid preparations may be in the form of, for example, aqueous or oily suspensions, solutions, emulsions, syrups, or elixirs, or may be presented as a dry product for constitution with water or other suitable vehicle before use. Such liquid preparations may contain conventional additives such as suspending agents, non-aqueous vehicles (which may include edible oils), or preservatives.

The compounds according to the invention may also be formulated for parental administration (e.g. by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by aseptic isolation of sterile solid or by lyophilization from solution, for constitution with a suitable vehicle, e.g. sterile, pyrogen free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouth washes comprising the active ingredient in a suitable liquid carrier. For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are possibly presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams, or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation the compounds according to the invention are conveniently delivered from an insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin of blister packs from which the powder may be administered with the aid of an inhalator or insufflator.

When desired the above described formulations adapted to give sustained release of the active ingredient may be employed.

The compounds and pharmaceutical compositions of the invention may also be used in combination with other therapeutic agents.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician. In general, however, a suitable dose will be in the range of from about 0.1 to 300 mg/kg of bodyweight per day, particularly from about 1 to 100 mg/kg of bodyweight per day. An appropriate dosage unit involved in oral administration may generally contain from about 1 to 250 mg, particularly from about 25 to 250 mg, of a compound of formula (I). The dosage employed for the topical administration will, of course, depend on the size of the area being treated. For the eyes each dose will be typically in the range of from 10 to 100 mg of the compound of formula (I).

For use in the treatment of PPAR related disorders the compounds of the invention can be administered by any of the aforementioned routes, particularly by the oral route or by injection. The daily dosage for a 70 kg mammal will be in the range of about 5 mg to 5 g of a compound of formula (I).

EXAMPLES

As used herein the symbols and conventions used in these examples are consistent with those used in the contemporary scientific literature, for example, the Journal of Medicinal Chemistry.

Example 1

A transient cotransfection assay was used to screen for activators of PPARγ. As mammalian cell lines contain endogenous nuclear receptors that can complicate interpretation of the results, we used an established chimera system in which the ligand-binding domain of the murine PPARγ was fused to the DNA binding domain of the yeast transcription factor GAL4. The GAL4-PPARγ chimera was cotransfected into CV-1 cells with a reporter construct containing five copies of the GAL4 binding site upstream of the thymidine kinase promoter driving secreted placental alkaline phosphatase (SPAP) as reporter. Data is seen in the table below.

Plasmids

GAL4-PPAR chimeras and UAS-tk-CAT/SPAP reporters. The GAL4-PPAR expression constructs contain the translation initiation sequence and amino acids 1–76 of the human glucocorticoid receptor fused to a nucleotide sequence encoding for amino acids 1–147 of GAL4 in the pSG5 expression vector (Stratagene). A nucleotide sequence encoding for amino acids 167–468, 138–440, and 174–475 of PPARα, NUC-1, and PPARγ1, respectively, were amplified by polymerase chain reaction (PCR) using vent polymerase (New England Biolabs) and inserted C-terminal to the GAL4 sequences. The UAS-tk-CAT/SPAP reporters contain 5 copies of the GAL4 binding site inserted into pBLCAT2 or pG12-tk-SPAP (Luckow, B. et al, 1987 and Berger et al, 1988).

pSG-PPARs

Nucleotide sequences encoding for murine PPARα, NUC-1, and PPARγ were inserted into the expression vector pSG5 (Stratagene).

aP2-tk-CAT

The 518 bp EcoR1/Xba1 fragment containing the enhancer of the aP2 gene (Graves et al., 1992) was inserted into pBLCAT2 (Luckow and Schutz, 1987).

Transfection assay: SPAP reporter

CV-1 cells were plated in DME medium supplemented with 10% delipidated fetal calf serum at a density of $2.4 \times 10^4$ cells per well in a 96-well plate (Costar) 16–24 h before transfection. In general, 8.0 ng of reporter plasmid, 25.0 ng of β-galactosidase expression vector (pCH110, Pharamacia), and 2.0 ng of GAL4-PPARγ expression vector were mixed with carrier DNA (pBluescript, Stratagene) to a total of 80 ng of DNA per well in a volume of 10 μl optiME medium (GIBCO BRL). To this, a second mix, containing 9.3 μl optiME medium and 0.7 μl of LIPOFECTAMINE™ (GIBCO BRL), was added. After 30 min. an additional 80 μl of optiME medium were added and the combined mix was then applied to the cells. 16 h later the medium was exchanged to DME medium supplemented with 10% delipidated fetal calf serum and the test compound at a concentration of $10^{-5}$M. After incubation for an additional 24 h SPAP activity and β-galactosidase activity were measured as previously described (Pfahl et al., 1990).

Transfection assay: CAT reporter

CV-1 cells were plated in DME medium supplemented with 10% delipidated fetal calf serum at a density of $1.2 \times 10^5$ cells per well in a 24-well plate (Costar) 16–24 h before transfection. In general, 100 ng of reporter plasmid, 200 ng of β-galactosidase expression vector (pCH 110, Pharamacia), and variable amounts amounts of receptor expression vector were mixed with carrier DNA (pBluescript, Stratagene) to 500 ng of total DNA per well in a volume of 50 μl optiME medium (GIBCO BRL). To this mix, 50 μl of a 1:10 dilution of LIPOFECTAMINE™ (GIBCO BRL) in optiME medium was added. After 30 min. an additional 400 μl of optiME medium was added and the total mix applied to the cells. 16 h later, the medium was exchanged to DME medium supplemented with 10% delipidated fetal calf serum and the test compound at the indicated concentration. After incubation for an additional 24 h, chloramphenicol acetyl transferase (CAT) activity and β-galactosidase activity were measured as previously described (Pfahl et al., 1990). CAT activity was normalized for transfection efficiency by using the cotransfected β-galactosidase expression plasmid (pCH110, Pharmacia) as internal standard.

Northern analysis

C3H10T1/2 cells were seeded at a density of $2.5 \times 10^{-6}$ per 225 cm² flasks (Costar). 16 h later 0.1 % DMSO (vehicle), pioglitazone at $10^{-5}$M or the MHI differentiation cocktail (50 μM hydrocortisone, 0.5 mM 3-isobutyl-1-methylxanthine, 60 μM indometacin) was added. Medium was exchanged every three days and fresh compound added. Cells were harvested on day nine and poly (A)+RNA prepared using the PolyATract System 1000 (Promega). 41 μg of poly (A)+RNA were loaded per lane for Northern analysis.

Differentiation assay

C3H10T/1/2 cells were grown in DME medium (GIBCO BRL) supplemented with 10% fetal calf serum. Cells were plated at a density of 1.0×10⁵ cells per well in a 24-well plate (Costar). 16 h later, compound was added at the indicated concentration. Medium and compound were exchanged every three days. Cells were stained at day 7 with oil-red-O and photographed.

Results From Transfection Assay: SPAP Reporter.

| Compound | Fold Activation |
|---|---|
| 5-{4-[2-(Methyl-pyridine-2-yl-amino)-ethoxy]-benzyl}-thiazolidine-2,4-dione | 47.6 |
| 5-[4-(1-methyl-cyclohexylmethoxy)-benzyl)-thiazolidine-2,4-dione | 46.1 |
| 5-{4-[2-(5-Ethyl-pyridine-2-yl)-ethoxy]-benzyl}-thiazolidine-2,4-dione | 42.1 |
| 7-{2-[4-(1-Methyl-hexyl)-phenyl]-cyclopent-2-enyl}-heptanoic acid | 27.0 |
| 2-(6,6,9,9-tetramethyl-6,7,8,9-tterahydro-benzo[g]quinolin-3-yl)-benzoic acid | 25.9 |
| {4-Chloro-6-(2,3-dimethyl-phenylamino)-pyrimidin-2-ylsulfanyl}-acetic acid | 25.7 |
| 7-[43-Hydroxy-5-oxo-2-(3-oxo-oct-1-enyl)-cyclopentyl]-heptanoic acid | 25.6 |
| 7-{2-[4-(Cyclopentyl-hydroxy-methyl)-phenyl]-5-oxo-cyclopent-1-enyl}-heptanoic acid | 24.6 |
| 2-[3-Bromo-5-(2-butyl-4-chloro-5-ethoxycarbonylmethylcarbamoyl-imidazol-1-ylmethyl)-benzofuran-2-yl]-benzoic acid | 23.9 |
| 7-[5-Hydroxy-2-(3-hydroxy-oct-1-enyl)-3-oxo-cyclopentyl]-hept-5-enoic acid | 23.8 |
| (2-Phenyl-3-propyl-1H-indol-5-yl)-acetic acid | 21.7 |
| (3-phenethyl-2-phenyl-1H-indol-5-yl)-acetic acid | 21.2 |
| 5-[5-Hydroxy-4-(3-hydroxy-oct-1-enyl)-hexahydro-pentalen-2-ylidene]-pentanoic acid | 19.6 |
| 5-(2-Benzyl-chroman-6-ylmethyl)-thiazolidine-2,4-dione | 18.2 |
| [5-Dimethylamino-2-(4-dimethylamino-benzyl)-phenyl]-acetic acid | 17.8 |
| 9-[2-(4-Carboxy-butyl)-4,6-diisopropoxy-phenyl]-7-oxo-non-8-enoic acid | 11.3 |

Example 2

To test for direct interactions between thiazolidinediones and PPARγ, the ligand binding domain of PPARγ was expressed in *E. Coli* as a fusion protein with glutathionine-S-transferase (GST-PPARγ LBD). Radiolabeled 5-{4-[2-(Methyl-pyridine-2-yl-amino)-ethoxy]-benzyl}-thiazolidine-2,4-dione bound specifically and saturably to GST-PPARγ LBD with a $K_d$ of 43 nM. No binding was detected in extracts from bacteria expressing glutathione-S-transferase.

cDNA encoding amino acids 174 to 475 of PPARg1 was amplified via polymerase chain reaction and inserted into bacterial expression vector pGEX-2T (Pharmacia). GST-PPARγ LBD was expressed in BL21 (DE3)plysS cells and extracts prepared as previously described (Mangelsdorf, 1991).

Bacterial extracts containing the glutathione-S-transferase-PPARγ ligand binding domain fusion protein (GST-PPARγ LBD) were incubated with increasing concentrations of tritiated 5-{4-[2-(Methyl-pyridine-2-yl-amino)-ethoxy]-benzyl}-thiazolidine-2,4-dione (specific activity, 40 Ci/mmol) in the absence or presence (of a 500-fold excess of nontritiated 5-{4-[2-(Methyl-pyridine-2-yl-amino)-ethoxy]-benzyl}-thiazolidine-2,4-dione. Specific binding of tritiated 5-{4-[2-(Methyl-pyridine-2-yl- amino)-ethoxy]-benzyl}-thiazolidine-2,4-dione to GST-PPARγ LBD was 14,500 dpm at 200 nM with a non-specific binding of 1,900dpm, and 13,500 dpm at 100 nM with a non-specific binding of 1,700 dpm.

For saturation binding analysis, bacterial extracts (100 μg protein) were incubated at 40° C. for 3 hr in buffer containing 10 mM Tris, pH 8.0, 50 mM KCl, 10 mM DTT with [³H]-5-{4-[2-(Methyl-pyridine-2-yl-amino)-ethoxy]-benzyl}-thiazolidine-2,4-dione (specific activity, 40 Ci/mmol) in the presence or absence of unlabeled 5-{4-[2-(Methyl-pyridine-2-yl-amino)-ethoxy]-benzyl}-thiazolidine-2,4-dione. Bound was separated from free radioactivity by elution through 1 ml Sephadex G-25 desalting columns (Boehringer Mannheim). Bound radioactivity eluted in the column void volume and was quantitated by liquid scintillation counting.

References

Berger, J., Hauber, R., Geiger, R., and Cullen, B. R. (1988) Secreted alkaline phosphatase: a powerful new quantitative indicator of gene expression in eukaryotic cells. Gene 66, 1–10.

Colca, J. R., and Morton, D. R. (1990) Antiyperglycemic thiazolidinediones: ciglitazone and its analogues, in New Antidiabetic Drugs (C. J. Bailey and P. R. Flatt, eds.). Smith-Gordon, New York, 255–261.

Chang, A. Y., Wyse, B. M., and Gilchrist, B. J. (1983) Ciglitazone, a new hypoglycemic agent. II. effect on glucose and lipid metabolism and insulin binding in the adipose tissue of C57BL/6J-ob/ob, and ± mice. Diabetes 32, 839–845.

Dreyer, C., Krey, G., Keller, H., Givel, F., Helftenbein, G., and Whali, W. (1992) Control of the peroxisomal b-oxidation pathway by a novel family of nuclear hormone receptors. Cell 68, 879–887.

Gottlicher, M., Widmark, E., Li, Q., and Gustafsson, J.-A. (1992) Fatty acids activate a chimera of the clofibrate acid-activated receptor and the glucocorticoid receptor. Proc. Natl. Acad. USA 89, 4653–4657.

Graves, R. A., Tontonoz, P., and Spiegelman, B. M. (1992) Analysis of a tissue specific enhancer: ARF6 regulates adipogenic gene expression. Mol. Cell. Biol. 12, 1202–1208.

Harris, P. K. W., and Kletzien, R. F. (1994) Localization of a pioglitazone response element in the adipocyte fatty acid binding protein gene. Mol. Pharmacol. 45, 439–445.

Hiragun, A., Sato, M., and Mitsui, H. (1988) readipocyte differentiation in vitr: identification of a highly active adipogenic agent. J. Cell Physiol. 134, 124–130.

Isseman, I., and Green, S. (1990) Activation of a member of the steroid hormone receptor superfamily by peroxisome proliferators. Nature 347, 645–650.

Keller, H., and Whali, W. (1993) Peroxisome proliferator-activated receptors: a link between endocrinology and nutrition? Trends Endocrin. Met. 4, 291–296.

Kleitzien, R. F., Clarke S. D., and Ulrich, R. G. (1992) Enhancement of adipocyte differentiation by an insulin-sensitizing agent. Mol. Pharmacol. 41, 393–398.

Kliewer, S. A., Forman, B., Blumberg, B., Ong. E. S, Borgmeyer, U., Mangelsdorf, D. J., Umesono, K., and Evans, R. M. (1994) Differential expression and activation of a family of murine peroxisome proliferator-activated receptors. Proc. Natl. Acad. Sci. USA 91, 7355–7359.

Luckow, B., and Schutz, G. (1987) CAT constructions with multiple unique restriction sites for the functional analysis of eukaryotic promoters and regulatory elements. Nuc. Acid Res. 15, 5490–5498.

Mangelsdorf, D. J. et al. (1991) Cell 66, 555–561.

Nolan, J. J., Ludvik, B., Beerdsen, P., Joyce, M., and Olefsky, J. (1994) Improvement of glucose tolerance and insulin resistance in obese subjects treated with troglitazone. N. Eng. J. Med. 331, 1188–1193.

Pfahl, M., Tzukerman, M., Zhang, X.-K., Lehmann, J. M., Hermann, T., Wills, K. N. and Graupner, G. (1990) Nuclear retinoic acid receptors: cloning, analysis, and function. Methods Enzymo. 26, 256–270.

Schmidt, A., Endo, N., Rutledge, S. J., Vogel, R., Shinar, D., and Rodan, G. A. (1992) Identification of a new member of the steroid receptor superfamily that is activated by a peroxisome proliferator and fatty acids. Mol. Endocrinol. 6, 1634–1641.

Sparks, R. L., Strauss, E. E., Zygmunt, A. I., and Phelan, T. E. (1991) Antidiabetic AD4743 enhances adipocyte differentiation of 3T3 T mesenchymal stem cells. J. Cell. Physiol. 146, 101–109.

Tontonoz, P., Hu, E., Graves, R. A., Budavari, A. I., and Spiegelman, B. M. (1994) mPPARg2:tissue-specific regulator of an adipocyte enhancer. Genes & Dev. 8, 1224–1234.

Williams, G. D., Deldar, A., Jordan, W. H., Gries, G., Long, G., and Dimarchi, R. D. (1993). Subchronic toxicity of the thiazolidinedione, Tanabe-174 (LY282449), in the rat and dog. Diabetes 42, Supplement 1, p. 59A.

Zhu, Y., Alvares, K., Huang, Q., Rao, M. S., and Reddy, J. (1993) Cloning of a new member of the peroxisome-proliferator activated receptor gene family from mouse liver. J. Biol. Chem. 268, 26817–26820.

What is claimed is:

1. A method for identifying compounds which will be useful for the treatment of diabetes, impaired glucose tolerance, obesity, or a cardiovascular disorder, comprising the step of determining whether the compound interacts directly with PPAR-gamma.

2. The method of claim 1 wherein said method is for identifying compounds which will be useful for the treatment of non-insulin-dependent diabetes.

3. The method of claim 1 wherein said step of determining comprises the step of specifically binding radiolabled 5-{4-[2-(Methyl-pyridine-2-yl-amino)-ethoxy]-benzyl}-thiazolidine-2,4-dione to the ligand binding domain of PPAR-gamma.

4. A method for treating diabetes, impaired glucose tolerance, obesity, or a cardiovascular disorder, comprising administration of a therapeutically effective amount of a compound which was identified by the method of claim 1.

5. The method of claim 4 wherein said method is for treating non-insulin-dependent diabetes.

6. The method of claim 4 wherein said cardiovascular disorder is atherosclerosis or hypertension.

7. The method of claim 4 wherein said compound is an activator of PPAR heterodimers with the retinoid X receptors.

8. A method for identifying compounds which will be useful for the treatment of diabetes, impaired glucose tolerance, obesity, or a cardiovascular disorder, comprising the step of determining whether the compound activates PPAR-gamma.

9. The method of claim 8 wherein said method is for identifying compounds which will be useful for the treatment of non-insulin-dependent diabetes.

10. The method of claim 8 wherein said step of determining comprises the step of specifically binding radiolabled 5-{4-[2-(Methyl-pyridine-2-yl-amino)-ethoxy]-benzyl}-thiazolidine-2,4-dione to the ligand binding domain of PPAR-gamma.

11. A method for treating diabetes, obesity, or a cardiovascular disorder, comprising administration of a therapeutically effective amount of a compound which was identified by the method of claim 8.

12. The method of claim 11 wherein said method is for treating non-insulin-dependent diabetes.

13. The method of claim 11 wherein said cardiovascular disorder is atherosclerosis or hypertension.

14. The method of claim 11 wherein said PPAR gamma activating compound is an activator of PPAR heterodimers with the retinoid X receptors.

* * * * *